United States Patent
Matejka et al.

(10) Patent No.: US 8,619,260 B2
(45) Date of Patent: Dec. 31, 2013

(54) MULTI-GRATING BIOSENSOR FOR LABEL-INDEPENDENT OPTICAL READERS

(75) Inventors: Steven R Matejka, Beaver Dams, NY (US); Robert Adam Modavis, Painted Post, NY (US); David Andrew Pastel, Horseheads, NY (US); Garrett Andrew Piech, Corning, NY (US); Christopher L. Timmons, Big Flats, NY (US)

(73) Assignee: Corning Incorporated, Corning, NY (US)

( * ) Notice: Subject to any disclaimer, the term of this patent is extended or adjusted under 35 U.S.C. 154(b) by 519 days.

(21) Appl. No.: 12/915,856

(22) Filed: Oct. 29, 2010

(65) Prior Publication Data

US 2011/0102799 A1    May 5, 2011

Related U.S. Application Data

(60) Provisional application No. 61/257,058, filed on Nov. 2, 2009, provisional application No. 61/386,708, filed on Sep. 27, 2010.

(51) Int. Cl.
*G01N 21/55* (2006.01)
*G01J 3/30* (2006.01)
*G01J 3/28* (2006.01)

(52) U.S. Cl.
USPC .................. 356/448; 356/317; 356/326

(58) Field of Classification Search
USPC ......... 356/399–401, 614–624, 317, 326, 318, 356/448; 436/164–172; 422/82.05–82.09; 385/12; 250/237 G
See application file for complete search history.

(56) References Cited

U.S. PATENT DOCUMENTS

| | | | |
|---|---|---|---|
| 7,454,094 B2 | 11/2008 | Gollier et al. | 385/12 |
| 7,497,992 B2 | 3/2009 | Cunningham et al. | 422/82.05 |
| 7,534,578 B1 | 5/2009 | Baird et al. | 435/7.4 |
| 7,599,055 B2 | 10/2009 | Gollier et al. | 356/246 |
| 2003/0133640 A1* | 7/2003 | Tiefenthaler | 385/12 |
| 2006/0062509 A1* | 3/2006 | Krol et al. | 385/12 |

(Continued)

FOREIGN PATENT DOCUMENTS

| | | | |
|---|---|---|---|
| EP | 1 031 828 A1 | 2/1999 | G01N 21/77 |
| WO | 2005/118143 A2 | 12/2005 | B01L 3/12 |

OTHER PUBLICATIONS

Dubendorfer, et al., "Sensing and Reference Pads for Integrated Optical Immunosensors", Journal of Biomedical Optics 2 (4), pp. 391-400, (Oct. 1997).

*Primary Examiner* — Roy M Punnoose
*Assistant Examiner* — Dominic J Bologna
(74) *Attorney, Agent, or Firm* — John L. Haack

(57) ABSTRACT

A multi-grating resonant waveguide (RWG) biosensor for an optical reader system having a spatial resolution limit is disclosed. The multi-grating RWG biosensor includes one or more signal-grating regions and one or more reference-grating regions. The multi-grating RWG biosensor can also include a non-resonance region that spatially separates the one or more signal-grating regions, that spatially separates the one or more reference-grating regions, and that spatially separates the one or more reference-grating regions from the one or more signal-grating regions. The non-resonance region can have a minimum width greater than the optical reader system spatial resolution limit. The RWG biosensor can have an asymmetric split-grating configuration. Methods of measuring a signal resonant wavelength of a multi-grating RWG biosensor using an optical reader having a spatial resolution limit are also disclosed.

33 Claims, 12 Drawing Sheets

(56) References Cited

U.S. PATENT DOCUMENTS

2006/0141611 A1* 6/2006 Frutos et al. ............... 435/287.2
2007/0202543 A1* 8/2007 Gollier et al. .................. 435/7.1
2007/0211245 A1* 9/2007 Pastel et al. .................. 356/246
2009/0032690 A1 2/2009 Modavis .................. 250/227.27
2009/0079976 A1* 3/2009 Cunningham et al. ........ 356/246
2009/0142790 A1* 6/2009 Fang et al. ..................... 435/29

* cited by examiner

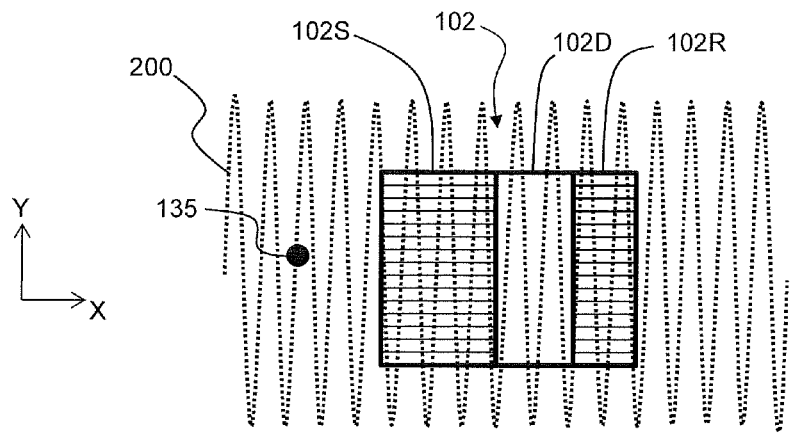
FIG. 13
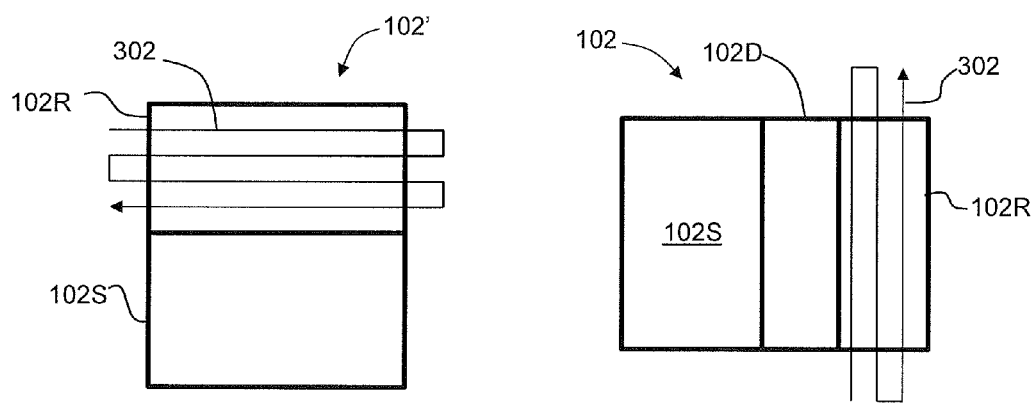
FIG. 14A
PRIOR ART
FIG. 14B

MULTI-GRATING BIOSENSOR FOR LABEL-INDEPENDENT OPTICAL READERS

CLAIMING BENEFIT OF PRIOR FILED U.S. APPLICATIONS

This application claims the benefit of U.S. Pat App. Ser. No. 61/257,058, entitled "MULTI-GRATING BIOSENSOR FOR LABEL-INDEPENDENT OPTICAL READERS," filed Nov. 2, 2009. This application also claims the benefit of U.S. Pat App. Ser. No. 61/386,708, entitled "MULTI-GRATING BIOSENSOR FOR LABEL-INDEPENDENT OPTICAL READERS," filed Sep. 27, 2010. The content of these documents and the entire disclosure of any publication or patent document mentioned herein is incorporated by reference.

CROSS-REFERENCE TO RELATED CO-PENDING APPLICATION

This application is related to commonly owned and assigned co-pending application U.S. Pat App. Ser. No. 61/257,061, entitled "MULTI-WAVELENGTH REFERENCE MICROPLATE FOR LABEL-INDEPENDENT OPTICAL READER."

FIELD

The present disclosure relates to biosensors used in label-independent optical readers, and in particular relates to such biosensors having multiple, spatially separated gratings.

BACKGROUND

Label-independent detection (LID) based optical readers can be used to detect drug binding to a target molecule such as a protein, or changes in living cells as material is displaced within a cell in response to a drug. Certain types of LID optical readers measure changes in refractive index on the surface of a resonant waveguide grating (RWG) biosensor for an array of RWG biosensors. The individual RWG biosensors are located in respective wells of a microplate. Spectrally broadband light from a light source is directed to each RWG biosensor. Only light whose wavelength is resonant with the RWG biosensor is strongly reflected. This reflected light is collected and spectrally analyzed to determine the resonant wavelength, with shifts in wavelength being representative of refractive index changes from biomolecular binding to the RWG biosensor, or similarly representing material displacements within cells immobilized to the sensor surface.

The repeatability of the resonant wavelength measurements depends on the precise positioning of the interrogation beam relative to the RWG sensor. This can require the optical reader to have an active positioning system for the microplate, which makes the reader expensive and complex. An alternative solution is to have a large interrogation beam that captures all of the information from the sensor. However, this results in problems distinguishing information from the "signal" biosensor from that of the "reference" biosensor.

SUMMARY

An aspect of the disclosure is a multi-grating RWG biosensor for an optical reader system having a spatial resolution limit. The multi-grating RWG biosensor includes one or more signal-grating regions and one or more reference-grating regions. The multi-grating RWG biosensor also includes a non-resonance region that spatially separates the one or more signal-grating regions, that spatially separates the one or more reference-grating regions, and that spatially separates the one or more reference-grating regions from the one or more signal-grating regions. The non-resonance region has a minimum width greater than the optical reader system spatial resolution limit. The RWG biosensor can have an asymmetric split-grating configuration.

Another aspect of the disclosure is a method of measuring a signal resonant wavelength of a RWG biosensor using an optical reader having a spatial resolution limit. The method includes operably disposing in a well of a microplate the RWG biosensor having spatially separated signal grating and reference-grating regions with a non-resonance region in between, wherein the non-resonance region has a minimum width greater than the optical reader spatial resolution limit. The method also includes irradiating the signal-grating region with the incident optical beam without touching the reference-grating region and generating reflected signal light. The method further includes spectrally analyzing the reflected signal light to obtain the signal resonant wavelength.

Another aspect of the disclosure is a method of measuring a signal resonant wavelength of a RWG biosensor using an optical reader having a spatial resolution limit. The method includes operably disposing in a well of a microplate the RWG biosensor having spatially separated signal-grating and reference-grating regions with a non-resonance region in between, wherein the non-resonance region has a minimum width greater than the optical reader spatial resolution limit. The method also includes simultaneously irradiating the signal-grating region, the reference-grating region and the non-resonance region with incident light to generate reflected light. The method further includes establishing from the reflected light, a reflected signal component from the signal-grating region, a dark component from the non-resonance region, and a reflected reference component from the reference grating region. The method additionally includes spectrally analyzing the reflected signal component to obtain the signal resonant wavelength.

These and other aspects of the disclosure will be further understood and appreciated by those skilled in the art by reference to the following written specification, claims and appended drawings.

BRIEF DESCRIPTION OF THE DRAWINGS

A more complete understanding of the present disclosure may be had by reference to the following detailed description when taken in conjunction with the accompanying drawings, wherein:

FIG. 13 illustrates an example asymmetric split-grating RWG biosensor along with a scan path that scans a light spot in the x-direction while oscillating in the y-direction;

FIG. 14A is a schematic view of a prior art RWG biosensor that has the conventional arrangement of the reference-grating region and the signal-grating region, and showing the ink-jet scanning path associated with forming the reference-grating region;

FIG. 14B is a schematic view of an asymmetric split-grating RWG biosensor and showing the simplified ink jet scanning path associated with forming the reference-grating region.

DETAILED DESCRIPTION

Reference is now made to embodiments of the disclosure, exemplary embodiments of which are illustrated in the accompanying drawings.

In the discussion below, reference is made to the optical reader system having a "resolution limit," which is a threshold value representing a minimum spatial dimension resolvable by the system. In the case of a scanning optical reader system that has an associated light spot, the resolution limit is defined by the light spot size. In the case of a non-scanning optical reader system that simultaneously captures reflected light using an image sensor such as a digital camera, the resolution limit is defined by the size and number of the image-sensor pixels needed to distinguish the non-resonance region that separates adjacent signal-generating or "resonance" regions.

Figure 1:
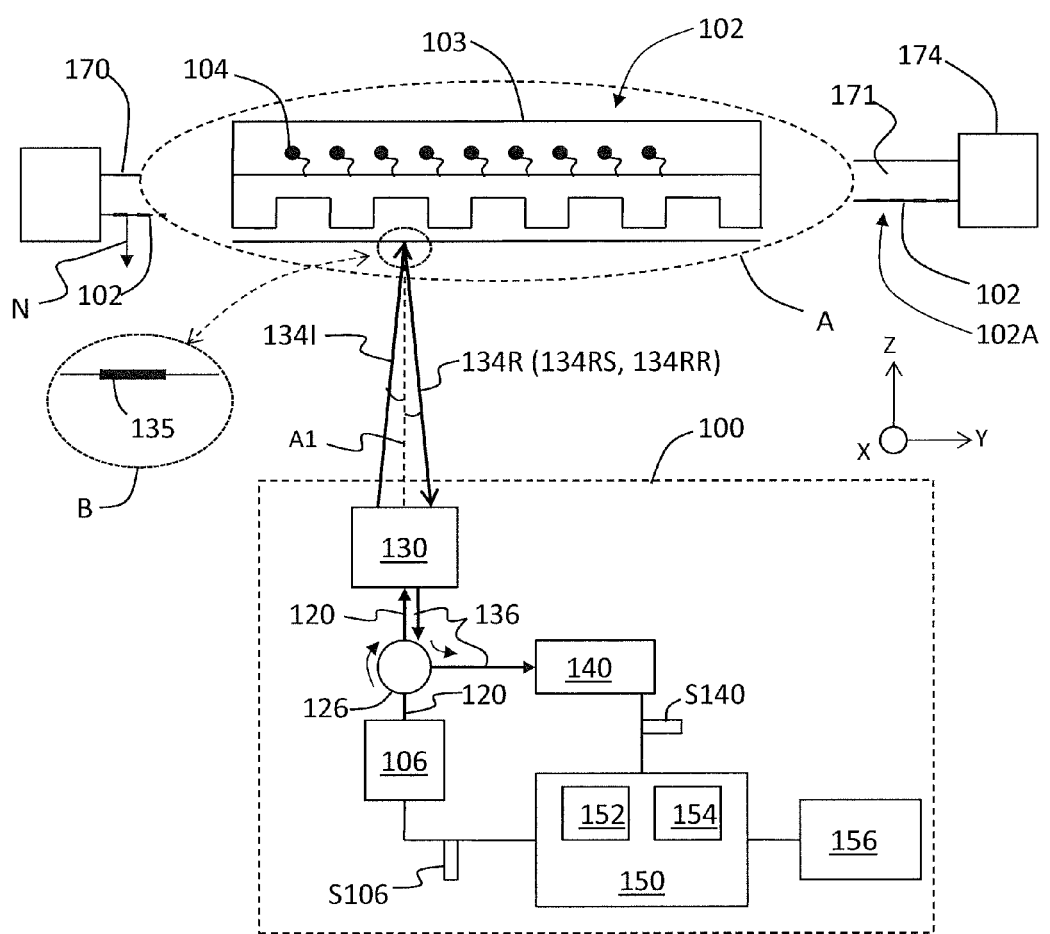
FIG. 1 is a generalized schematic diagram of an example optical reader system suitable for use with the multi-wavelength reference microplate of the disclosure.

FIG. 1 is a generalized schematic diagram of an example optical reader system ("system") 100 used to interrogate one or more resonant waveguide (RWG) biosensors 102 each having a surface 103 to determine if a biological substance 104 is present on the RWG biosensor. Inset A shows a close-up of an exemplary RWG biosensor 102.

Figure 2:
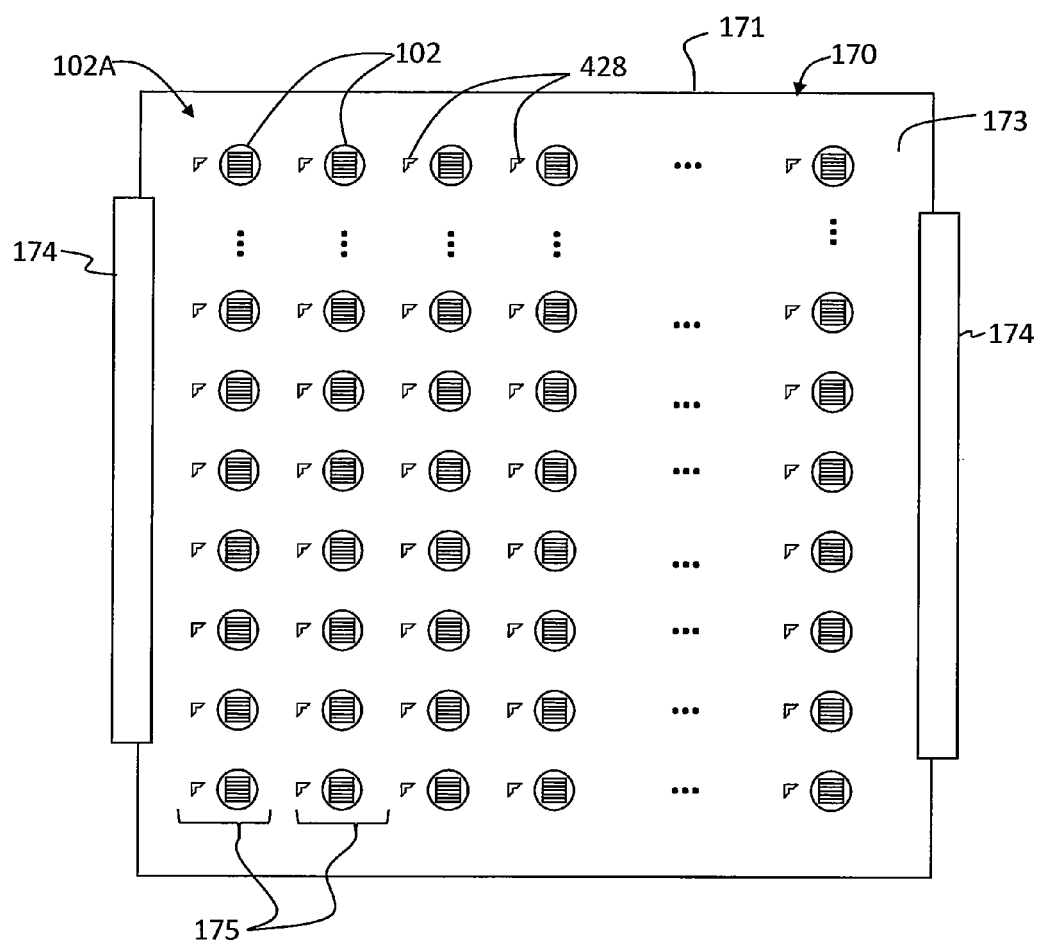
FIG. 2 shows an exemplary RWG biosensor array operably supported in regions or "wells" of a microplate, which in turn is held by a microplate holder.

FIG. 2 is a plan view of an example microplate 170 that comprises a support plate 171 with a surface 173 having a plurality of wells 175 formed therein. An example support plate 171 has a two-part construction of an upper plate and a lower plate (not shown), as described for example in U.S. Patent Application Publication No. 2007/0211245.

Microplate 170 of FIG. 2 illustrates an exemplary configuration where RWG biosensors 102 are arranged in an array 102A and operably supported in wells 175. An exemplary RWG biosensor array 102A has a 4.5 mm pitch for RWG biosensors 102 that are 2 mm square, and includes 16 RWG biosensors per column and 24 RWG biosensors in each row. In embodiments, fiducials 428 are used to position, align, or both, the microplate 170 in system 100. A microplate holder 174 is also shown holding microplate 170. Many different types of plate holders can be used as a microplate holder 174.

With reference again to FIG. 1, system 100 includes a light source 106 that generates light 120. Light source 106 may include one or more of a lamp, laser, diode, filters, attenuators, etc. An example light source 106 includes a broad-band light source such as a super luminescent diode (SLD). Light 120 from light source 106 is directed by a coupling device 126 (e.g., a circulator, optical switch, fiber splitter or the like) to an optical system 130 that has an associated optical axis A1 and that transforms light 120 into an incident optical beam (incident light) 134I, which forms a light spot 135 at RWG biosensor 102 (see inset B). Incident optical beam 134I (and thus light spot 135) is scanned over the RWG biosensor 102 by either a scanning operation of scanning optical system 130 or by the movement of microplate 170 via microplate holder 174.

Incident optical beam 134I reflects from RWG biosensor 102, thereby forming a reflected optical beam (reflected light) 134R. Reflected optical beam 134R is received by optical system 130 and light 136 therefrom (hereinafter, "guided light signal") is directed by coupling device 126 to a spectrometer unit 140, which generates an electrical signal S140 representative of the spectra of the reflected optical beam. In embodiments, a controller 150 having a processor unit ("processor") 152 and a memory unit ("memory") 154 then receives electrical signal S140 and stores in the memory the raw spectral data, which is a function of a position (and possibly time) on RWG biosensor 102. Thereafter, processor 152 analyzes the raw spectral data based on instructions stored therein or in memory 152.

Figure 3:
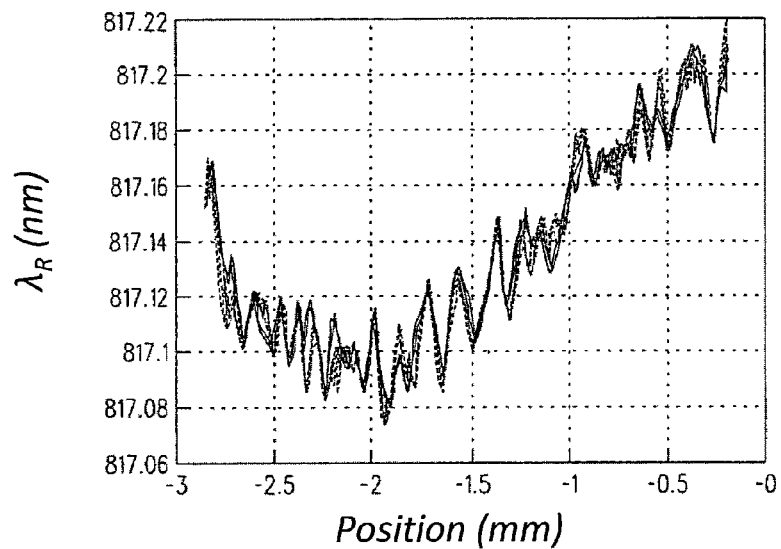
FIG. 3 is an example plot of the reflected resonant wavelength $\lambda_R$ (nm) vs. position (mm) across the RWG biosensor.

The result is a spatial map of resonant wavelength ($\lambda_R$) data such as shown in FIG. 3, which shows the calculated resonance wavelength centroid as a function of the position light spot 135 as it moves across the sensor for a number of different scans. The variation of the resonance wavelength $\lambda_R$ indicates if a chemical or biological reaction happened for a specific RWG biosensor 102. FIG. 3 also shows the positional sensitivity of the resonant wavelength measurement.

In embodiments, controller 150 includes or is operably connected to a display unit 156 that displays measurement information such as spectra plots, resonant wavelength plots, and other measurement results, as well as system status and performance parameters. In embodiments, spectra can be processed immediately so that only the resonant wavelengths (as calculated, for example, as the respective centroids of measured spectra) are stored in memory 154.

Figure 4:
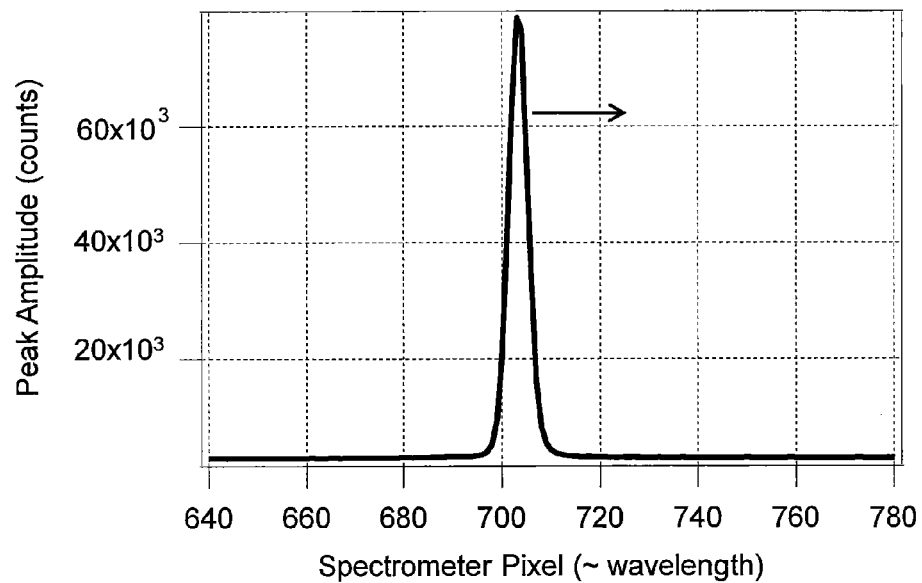
FIG. 4 is a plot of the reflected resonant peak amplitude (photon counts) versus spectrometer pixel location, which corresponds to wavelength.

The most commonly used technique for measuring biochemical or cell assay events occurring on RWG biosensors 102 is spectral interrogation. Spectral interrogation entails illuminating RWG biosensor 102 with a multi-wavelength or broadband beam of light (incident optical beam 134I), collecting the reflected light (reflected optical beam 134R), and analyzing the reflected spectrum with spectrometer unit 140. An exemplary reflection spectrum from an example spectrometer unit 140 is shown in FIG. 4, where the "peak amplitude" is the number of photon counts as determined by an analog-to-digital (A/D) converter in the spectrometer. When chemical binding occurs at RWG biosensor surface 103, the resonance shifts slightly in wavelength, as indicated by the arrow, and such shift is detected by spectrometer unit 140.

Example RWG biosensors 102 make use of changes in the refractive index at sensor surface 103 that affect the waveguide coupling properties of incident optical beam 134I and reflected optical beam 134R to enable label-free detection of biochemical substance 104 (e.g., cell, molecule, protein, drug, chemical compound, nucleic acid, peptide, carbohydrate) on the RWG biosensor. A biochemical substance 104 may be located within a bulk fluid deposited on RWG biosensor surface 103, and the attachment of this biochemical substance to the sensor surface alters the index of refraction at the RWG.

To detect biochemical substance 104, RWG biosensor 102 is probed with incident optical beam 134I, and reflected optical beam 134R is received at spectrometer unit 140. Controller 150 is configured (e.g., processor 152 is programmed) to determine if there are any changes (e.g., 1 part per million) in the RWG biosensor refractive index caused by the presence of biological substance 104. In embodiments, RWG biosensor surface 103 can be coated with, for example, biochemical compounds (not shown) that only allow surface attachment of specific complementary biochemical substances 104 such as antibodies or proteins, thereby enabling RWG biosensor 102 to be both highly sensitive and highly specific. In this way, system 100 and RWG biosensor 102 can be used to detect a wide variety of biological substances 104. Likewise, RWG biosensor 102 can be used to detect the movements or changes in cells immobilized to RWG biosensor surface 103, for example, when the cells move relative to the RWG biosensor or when they incorporate or eject material, a refractive index change occurs.

If multiple RWG biosensors 102 are operably supported as an array 102A in wells 175 of microplate 170, which in turn is supported by microplate holder 174, then they can be used to enable high-throughput drug or chemical screening studies. For a more detailed discussion about the detection of a biological substance 104 (or a biomolecular binding event) using scanning optical reader systems, reference is made to U.S. patent application Ser. No. 11/027,547. Other optical reader systems are described in U.S. Pat. No. 7,424,187 and U.S. Patent Application Publications No. 2006/0205058 and 2007/0202543.

RWG biosensor typically includes a "signal" region 102S where chemical binding occurs at RWG biosensor surface 103, and a "reference" region 102R where no chemical binding occurs (e.g., the RWG grating is chemically deactivated). The resonant wavelength is generally referred to as $\lambda_R$, while the "signal" resonant wavelength is denoted as $\lambda_{RS}$ and the "reference" resonant wavelength of reference-grating region 102R is referred to as $\lambda_{RR}$. The reference-grating region is typically formed by chemically deactivating a region of RWG biosensor surface 103, resulting in contiguous signal- and reference-grating regions 102R and 102S. As discussed above, in the case where incident optical beam 134I is sufficiently large (i.e., as a large light spot 135) or where a smaller light spot 135 is scanned over the entire signal-grating region 102S, any overlap of the light spot with the reference-grating region 102R while scanning the signal-grating region leads to a confounded result and hence an inaccurate reading.

Spatially Separated Signal and Reference Gratings

Figure 5:
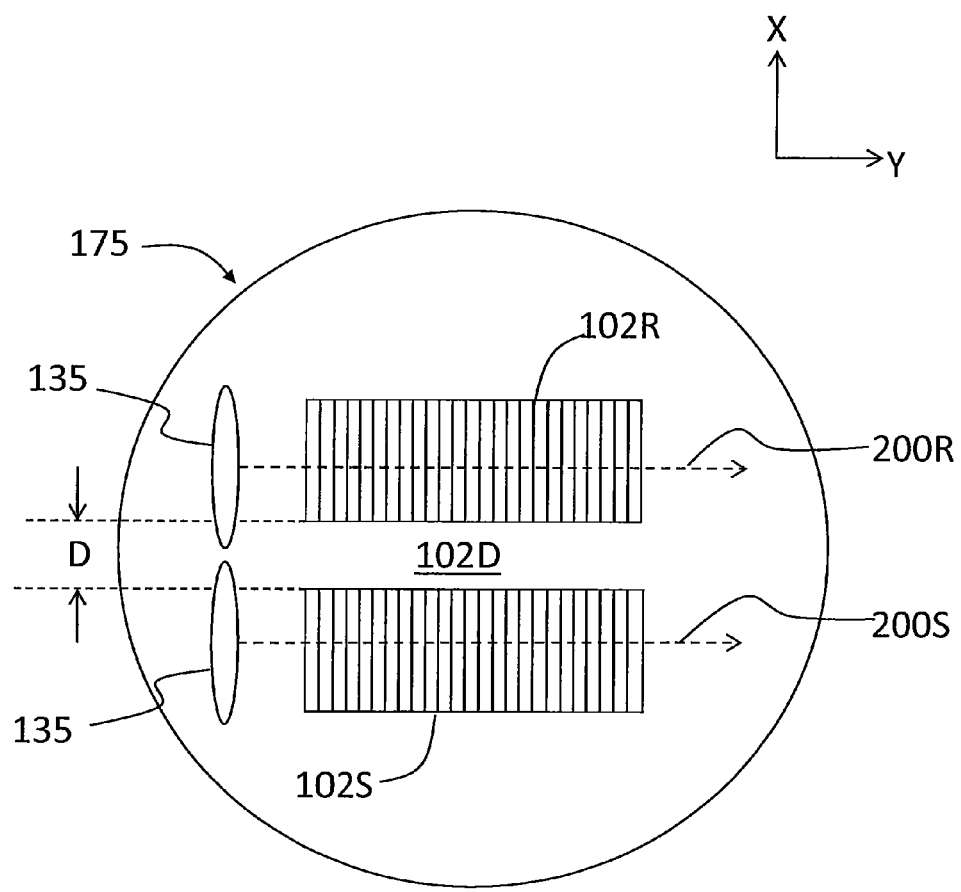
FIG. 5 is a plan view of a well that includes an example multi-grating RWG biosensor having signal- and reference-grating regions spatially separated from one another by a non-reflective region, and also shows example linear scan paths of a relatively large elliptical light spot.

FIG. 5 is a plan view of a well 175 that includes an example multi-grating RWG biosensor 102 having a signal-grating region 102S and a reference-grating region 102R spatially separated from one another by a non-resonance region 102D having a width D. This "split configuration" for the signal- and reference-grating regions allows the LID reader system to interrogate the full sensor regions—leading to minimal sensitivity to plate translation, and to physically distinguish the signals from the two regions.

Generally, RWG biosensor 102 has at least one signal-grating region 102S and at least one reference-grating region 102R, separated by a non-resonance reflective region 102D. In embodiments, non-resonance region 102D does not include a grating or like structure and is not an active sensor region, and therefore does not resonantly reflect incident light beam 134I in the manner of the RWGs of signal- and reference-grating regions 102S and 102R.

Alternatively, the non-resonance region 102D may be formed by keeping the original grating structure, but not waveguide-coating the region with the proper amount of high-refractive index material typically used for the sensor regions, so that the resonant wavelength in this region is completely eliminated or shifted out of the detection band of the reader system. In embodiments, while some amount of reflected light may originate from non-resonance region 102D when illuminated by incident light 134I, it is insubstantial when compared to the amount of reflected light 134RS from signal-grating regions 102S and reflected light 134RR from reference-grating region 102R. In embodiments, the non-resonance region 102D initially includes a grating and waveguide coating, but then a masking layer (not shown) is applied to define the non-resonance region. Examples of this masking approach are described in greater detail below.

In embodiments, non-resonance region 102D is a contiguous region and is described herein as a single region even though it may have one or more branches, be in the form of a grid pattern, or have what can be identified as one or more sub-regions. In embodiments, non-resonance region 102D surrounds at least one signal-grating region 102S and at least one reference-grating region 102R. The split configuration for signal-grating region 102S and reference-grating region 102R can be symmetric or asymmetric. Examples of different grating configurations for RWG biosensor 102 are discussed below.

In FIG. 5, light spot 135 is shown by way of example as elliptical with its major axis in the X-direction. Light spot 135 travels over a straight signal scan path 200S in the Y-direction over signal-grating region 102S and a straight reference scan path 200R in the Y-direction over reference-grating region 102R. Light spot 135 has a length in the X-direction larger than that of either signal- or reference-grating regions 102S and 102R so that some of the light spot extends into non-resonance region 102D. This ensures complete coverage of signal- and reference-grating regions 102S and 102R. It is also noted that the grating direction in signal- and reference-grating regions 102S and 102R can be either horizontal or vertical, and vertical is shown by way of example in FIG. 5.

Figure 6:
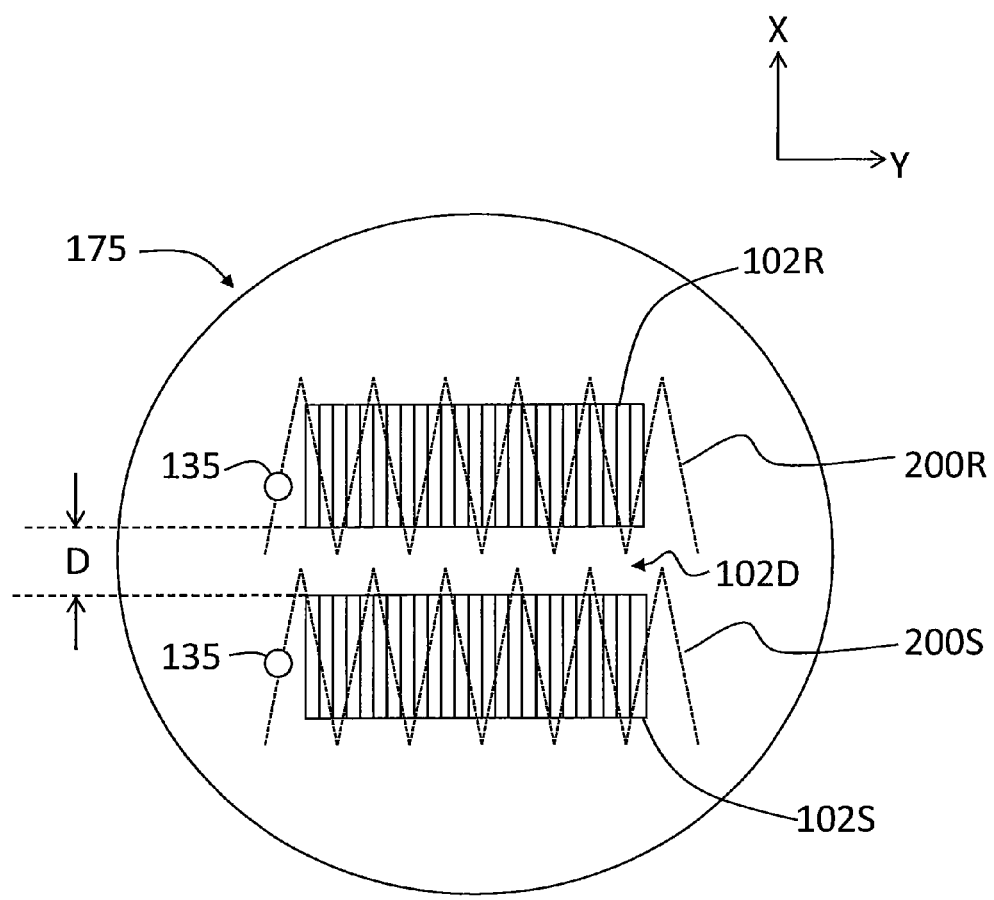
FIG. 6 is similar to FIG. 5, and shows an example of zig-zag scan paths of a relatively small round light spot.

FIG. 6 is similar to FIG. 5, except that light spot 135 is circular and relatively small (e.g., 20× smaller than the width of the RWG biosensor), and is scanned over respective zig-zag signal and reference scan paths 200S and 200R to cover substantially the entire signal- and reference-grating regions 102S and 102R. Note that the signal scan path 200S extends into non-resonance region 102D but does not touch reference-grating region 102R, and that reference scan path 200R extends into non-resonance region 102D but does not touch signal-grating region 102S. In embodiments, non-resonance region 102D has a minimum width D that greater than the size (i.e., diameter) of light spot 135. In embodiments, an example minimum width D can be 1.5× to 2.5× the width of light spot 135.

Generally, the size (width) of non-resonance region 102D is defined such that reflected light 134RS reflected by a signal-grating region 102S will not be mixed with reflected light 134RR from reference-grating region 102R. An example light spot diameter (e.g., at $1/e^2$ of the intensity) is between 25 microns and 250 microns, and more preferably is about 100 microns. Thus, for a light spot diameter of 100 microns, a minimum width D of between 100 to 250 microns ensures that light spot 135 does not illuminate both signal- and reference-grating region 102S and 102R at the same time. In embodiments where system 100 includes camera based imaging, then minimum width D is set such that one or more fully resolved camera pixels fit within non-resonance region 102D. In embodiments, minimum width D is greater than the resolution limit of system 100.

Other scan paths 200 can be used, such as multiple Y-direction paths at different X positions using a light spot diameter smaller than the size of either the signal-grating region 102S or reference-grating region 102R. The RWG biosensor 102 of the present disclosure is applicable to any optical interrogation method wherein one wishes to avoid the overlap of reflected light 134R from signal-grating region 102S and reference-grating region 102R. In embodiments, three to five "spectra" are collected from non-resonance region 102D, so that the minimum width D is selected accordingly based on the size of light spot 135.

In contrast to the scanned beam methods of interrogating a RWG described in FIG. 5 and FIG. 6, in other embodiments, system 100 is configured (e.g., via an imaging sensor or camera, not shown), to simultaneously capture reflected light 134RS from signal-grating region 102S and reflected light 134RR from reference-grating region 102R while receiving substantially no reflected light (at the grating resonance) from non-resonance region 102D. These regions are identified using signal-processing software operating in processor 152. In particular, reflected signal light 134RS (i.e., a reflected signal component), reflected reference light 134RR (i.e., a reflected reference component) and a "dark" signal component from non-resonance region 102D are determined from reflected light 134R. Note that an example imaging camera or sensor (e.g., CCD array camera or sensor) has pixels that can be used to identify the various components of the reflected light, including the "dark" signal component associated with pixels receiving substantially less light than other pixels. Here, the resulting digital image is digitally processed to identify the light components from signal-grating region 102S and reference-grating region 102R and the "dark" component of non-resonance region 102D.

Figure 7A:
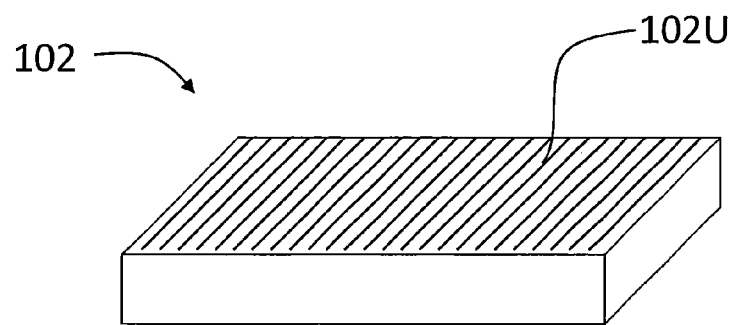
FIG. 7A is a perspective view and FIG. 7B is a plan view of an example RWG biosensor having a unitary grating structure.
Figure 7B:
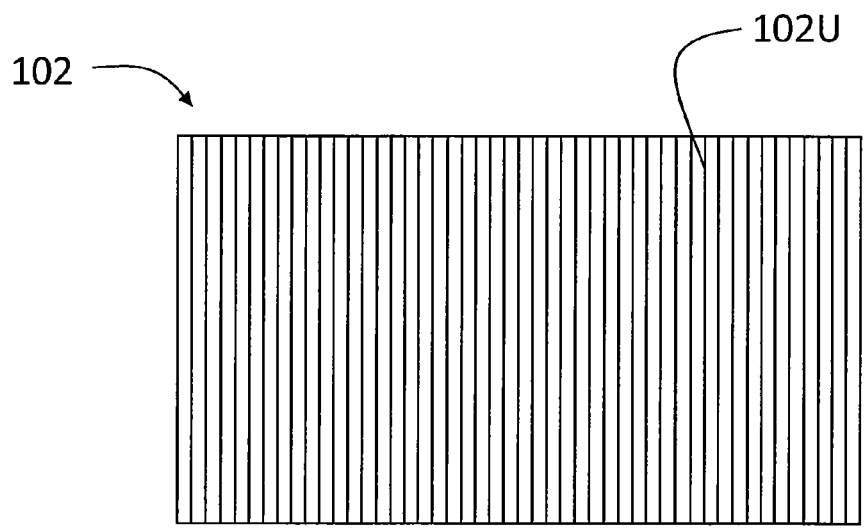
Figure 8A:
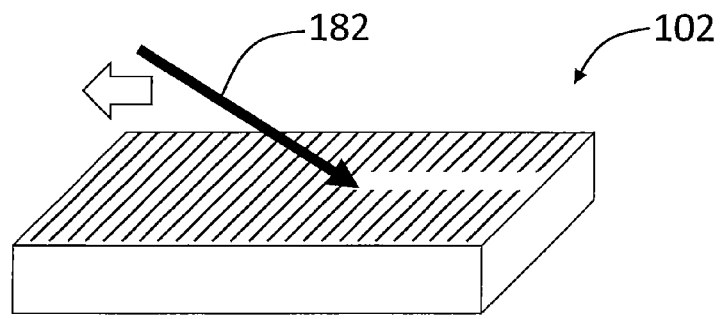
FIG. 8A is similar to FIG. 7A and illustrates the unitary grating being processed by a processing beam to remove a portion of the unitary grating to form the non-resonant region.
Figure 8B:
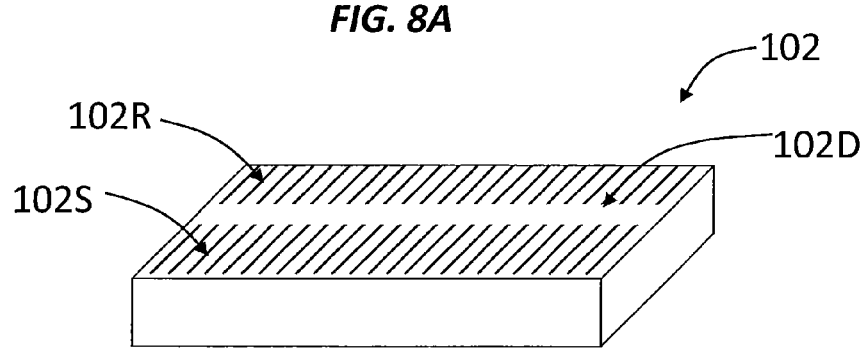
FIG. 8B is a perspective view and FIG. 8C is a plan view of the multi-grating RWG biosensor after the processing shown in FIG. 8A, or as formed directly using another process.
Figure 8C:
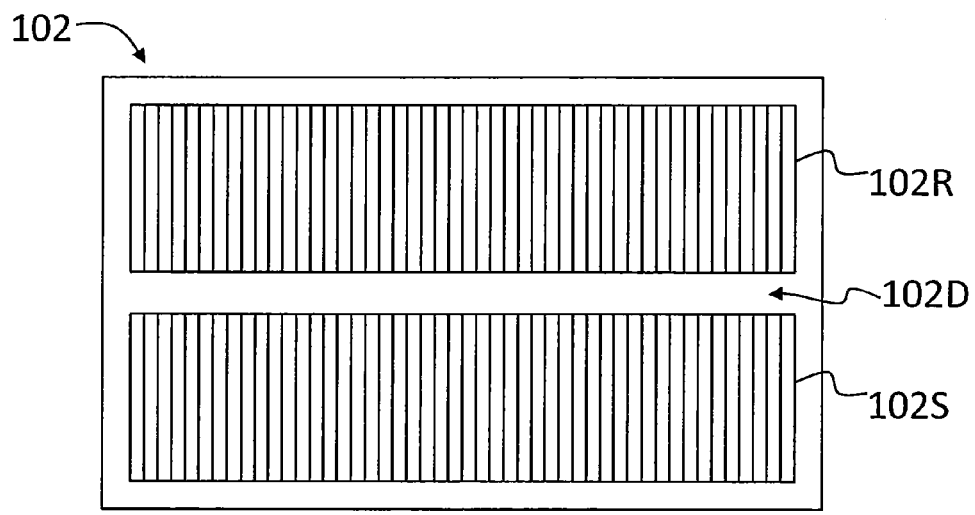

FIG. 7A is a perspective view and FIG. 7B is a plan view of an example RWG biosensor 102 having a single or unitary grating region 102U. In embodiments, multi-grating RWG biosensor 102 is formed with the single or unitary grating region 102U as in FIG. 7A and then the unitary grating region is divided into the signal- and reference-grating regions 102S and 102R. In embodiments, the dividing processing involves selectively removing grating material, and is accomplished using any one of a number of techniques, such as laser ablation, selective etching, ion milling, etc. FIG. 8A is a perspective view of the RWG biosensor of FIG. 7A being processed by a processing beam 182 (e.g., a laser beam, ion beam, etc.) to selectively remove a portion of the unitary grating 102U to form non-resonance region 102D. FIG. 8B and FIG. 8C are perspective and plan views respectively of the resulting multi-grating RWG biosensor.

In embodiments, a portion of unitary grating section 102U is selectively covered or "masked" to nullify the grating reflection to define non-resonance region 102D. This is accomplished, for example, by using selective coating techniques or strapping techniques to apply a patterned layer of blocking (masking) material on the underside of the microplate to define non-resonance region 102D. Such a blocking material prevents illumination from the light source from striking the region 102D. Examples of such blocking materials includes aluminum, silver, an adhesive layer, or any coating that is opaque to the illumination wavelength.

In embodiments, multi-grating RWG biosensor 102 is formed directly without first forming unitary grating region 102U. This is accomplished, for example, by using a suitably formed master (e.g., via electron-beam formation) that is used to form the signal, reference and non-resonant regions 102S, 102R and 102D into a suitable RWG grating substrate, via holographic exposure, via a lithographic process, or like process, such as ultraviolet (UV), cast and cure techniques, injection molding, stamping, etc., that directly form the non-grating non-resonant region 102D. Note that in this case, once the master is fabricated, that a masking element is not needed to define the separated signal- and reference-grating regions 102S and 102R. This reduces the need for careful alignment of a masking element with respect to RWG biosensor substrate (not shown), and also eliminates the mask cost.

Figure 9:
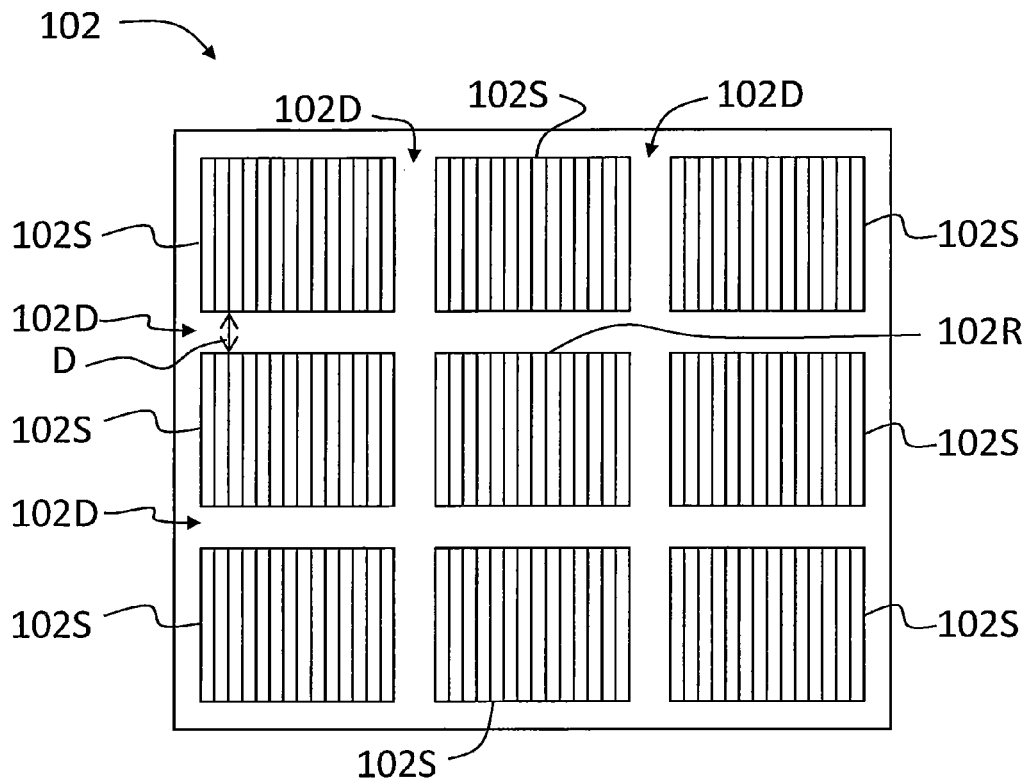
FIG. 9 is a plan view of an example multi-grating RWG biosensor having multiple signal-grating regions surrounding a central reference-grating region, wherein the non-resonant region has a grid-like geometry.

FIG. 9 is a plan view similar to FIG. 8C, except that the RWG biosensor 102 is formed in a manner that includes five signal-grating regions 102S and one reference-grating region 102R, all separated by a grid-type non-resonance region 102D. In the example configuration shown, reference-grating region 102R is in the center.

Figure 10:
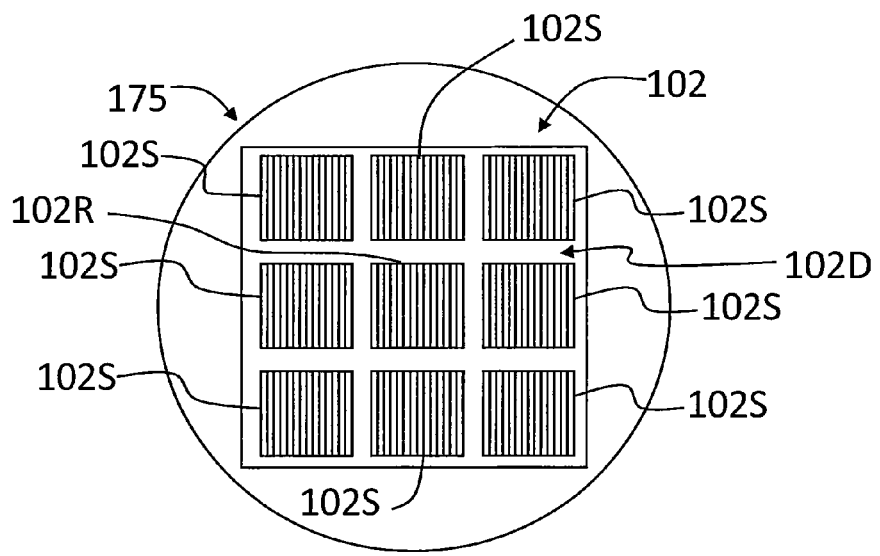
FIG. 10 is a plan view of the multi-grating RWG biosensor of FIG. 9 arranged in a well.
Figure 11:
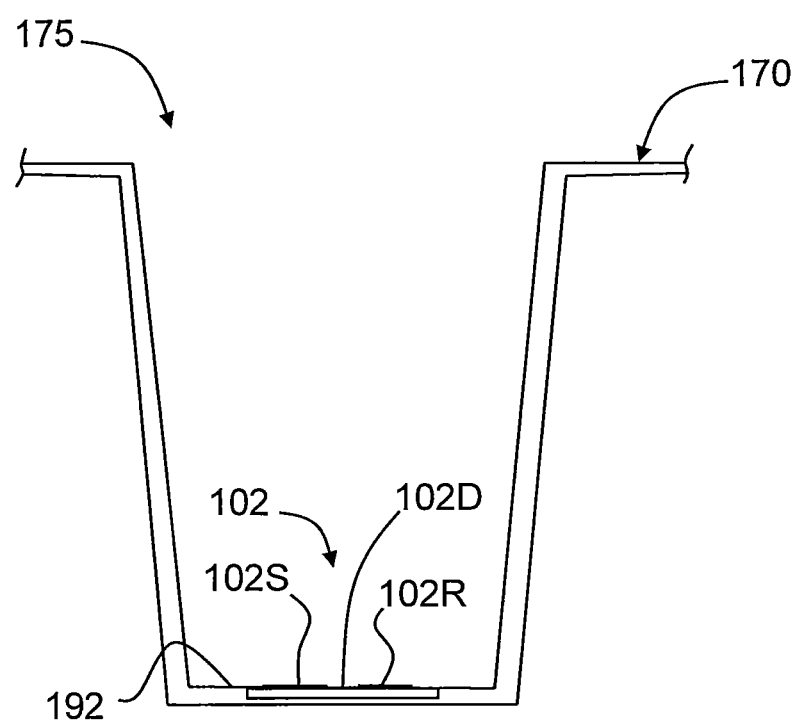
FIG. 11 is side cut-away view of a well showing a multi-grating RWG biosensor disposed at the bottom of the well.

FIG. 10 is a plan view of the multi-grating RWG biosensor 102 of FIG. 9 as arranged in well 175 that supports different biological materials 104 (see FIG. 1), with the multiple signal-grating regions 102S each configured to operably support (i.e., bind) one of the different biological substances. Such a biosensor configuration allows for multiple target biological material 104 to be immobilized on the different signal-grating regions 102S. This allows a multiplexed assay to be performed with a system 100 having essentially no translation (i.e. positional) sensitivity. FIG. 11 is a side view of multi-grating RWG biosensor 102 at a bottom 192 of well 175.

The present disclosure thus includes methods method of measuring a signal resonant wavelength of a multi-grating RWG biosensor 102 using optical reader system 100, which has a spatial resolution limit. One method includes operably disposing multi-grating biosensor 102 in well 175 of microplate 170. The method includes irradiating the signal-grating region 102S with incident optical beam 134I without touching the reference-grating region and generating reflected signal light 134RS. The method further includes spectrally analyzing reflected signal light 134RS to obtain the signal resonant wavelength $\lambda_{RS}$.

The method also optionally includes irradiating reference-grating region 102R with the incident optical beam 134I without touching signal-grating region 102S and generating reflected reference light 134RR, and then spectrally analyzing the reflected reference light to obtain the reference resonant wavelength $\lambda_{RR}$. The signal and reference resonant wavelengths can then be compared to establish if biochemical substance 104 has bound to signal-grating region 102S.

Asymmetric Split-Grating Configuration

The spatially separated (split) signal-grating region 102S and reference-grating region 102R need not be symmetrically arranged. In embodiments, at least one of the RWG biosensors 102 residing in one or more of wells 175 can have an asymmetric split-grating configuration.

Figure 12A:
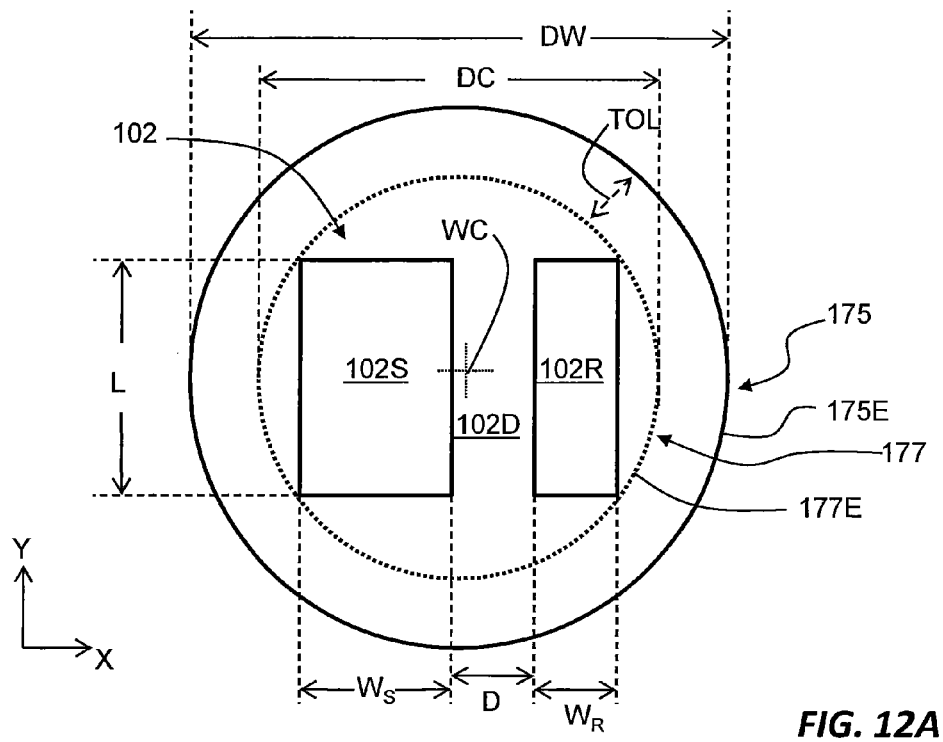
FIG. 12A is a schematic diagram of a first example asymmetric split-grating RWG biosensor shown residing with a well.

FIG. 12A illustrates a first example configuration of an asymmetric split-grating RWG biosensor 102, wherein the signal-grating region 102S has an area AS, the reference-grating region 102R has an area AR, and wherein these areas are different (i.e., AS≠AR. In an example, AS>AR.

Signal-grating region 102S has a length L and a width $W_S$, while reference-grating region also has length L but has a width $W_R$ that is less than width $W_S$ (note here that the two different grating regions need not have the same length L). Well 175 has a center WC, and an outer edge 175E with a diameter DW. The signal-grating region 102S and the reference-grating region 102R are asymmetrically circumscribed within a circular region 177 having an outer edge 177E and a diameter DC. Non-resonance region 102D has the aforementioned width D. There is an alignment tolerance TOL of the circular region 177 within well 175 given by the tolerable displacement of inner circular region outer edge 177E relative to well outer edge 175E. In an example, the difference in areas AS and AR that have the same length L results in the non-resonance region 102D not being centered on well center WC. This is advantageous for reasons discussed below.

Example values for the above dimensions can be: length L=1.2 mm, width $W_S$=0.8 mm, width $W_R$=D=0.4 mm, diameter DW=2.82 mm and diameter DC=2 mm. This type of asymmetric grating configuration for RWG biosensor 102 serves to minimize the area AR of reference-grating region 102R while ensuring that the non-resonance region 102D is not centered on well center 175C. An example alignment tolerances are TOL=0.4 mm or 0.42 mm.

Figure 12B:
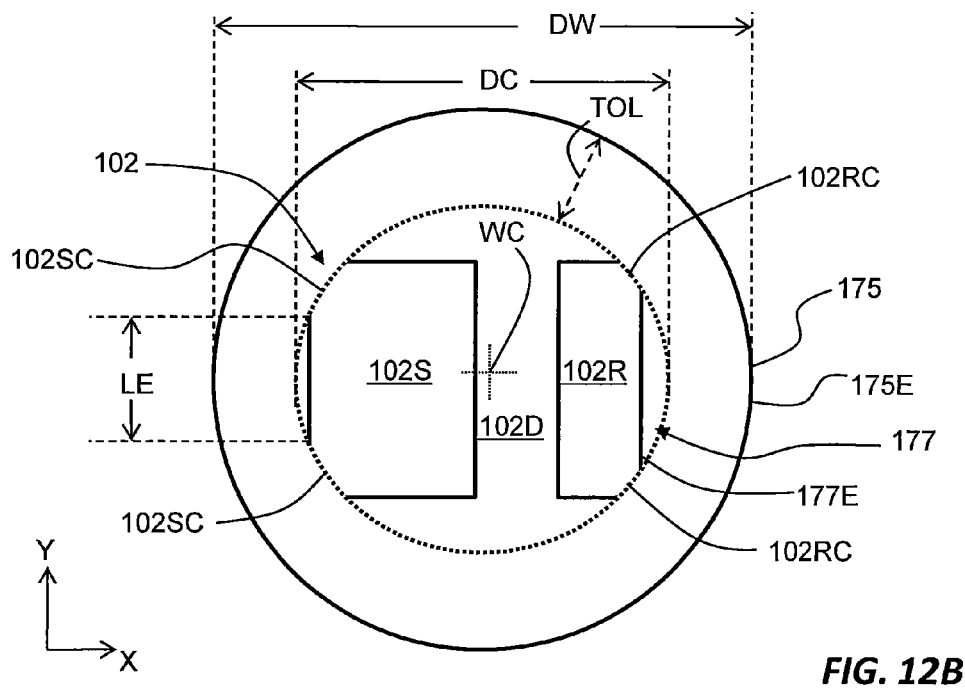
FIG. 12B is a schematic diagram of a second example asymmetric split-grating RWG biosensor shown residing with a well.

FIG. 12B is similar to FIG. 12A and illustrates a second example configuration of an asymmetric split-grating RWG biosensor 102 wherein the otherwise sharp outer corners of signal-grating region 102S and the reference-grating region 102R are rounded at outer edge 177E of circular region 177 to form rounded corners 102SC and 102RC, respectively. This defines an edge length LE (LE<L) for signal-grating region 102S and the reference-grating region 102R, as shown.

Example parameters associated with this second example configuration for asymmetric split-grating RWG biosensor 102 can be: edge length LE=0.8 mm, diameter DW=2.82 mm and diameter DC=1.79 mm. The configuration of FIG. 12B reduces the total amount of grating area in RWG biosensor 102 by 4%. However, the tolerance TOL for locating RWG biosensor 102 inside well 175 increases from TOL=0.42 mm to TOL=0.53 mm. This 20% increase in the positional tolerance of RWG biosensor 102 within well 175 can significantly improve the process capability for aligning the RWG biosensor within the well. If the tolerance TOL=0.42 mm can be maintained, the total sensor area of RWG biosensor 102 can be increased from 1.46 mm² to 1.63 mm² using the second example asymmetric split-grating RWG biosensor as illustrated in FIG. 12B.

Asymmetric split-grating RWG biosensors 102 can be fabricated using any of the known RWG biosensor fabrication techniques, including, for example, those mentioned above and nano-imprint lithography (UVCC) or DVD-like processing techniques. A glass master can be fabricated using electron beam lithography. The necessary grating patterns can be transferred directly to inserts using nano-imprint lithography with a UV curable thin film. Alternatively, the grating patterns can be replicated into a UV curable polymer using imprint lithography onto a thick glass substrate. This polymer replica can then used for fabricating electroformed replicas called stampers. These stampers are loaded into an injection mold for fabrication of inserts with grating sensors. Modification of the design requires fabrication of a new glass master via electron beam lithography.

FIG. 13 illustrates an example asymmetric split-grating RWG biosensor 102, along with a scan path 200 that scans light spot 135 in the x-direction while oscillating in the y-direction. Note that the signal-grating region 102S and the reference-grating region 102R are aligned in the scan direction. Minimal positional data is acquired during scanning, requiring a significant drop in power to be used to identify the leading edges of the signal and reference regions. In an example, setting D=400 microns for the non-resonance region 102D ensures that at least 2 to 3 pixels of low power are observed. This power drop signals the transition from the signal-grating region 102S to the reference-grating region 102R during scanning.

In embodiments, the widths $W_S$, D and $W_R$ are integer multiples of one another to simplify the data processing and analysis following the scan.

Certain reader systems 100 scan down the center of RWG biosensors 102. An example alignment tolerance between the center of incident optical beam 134I and the center of microplate 170 for such systems is +/−400 microns. Contributions to this alignment tolerance include insertion alignment to the microplate body and individual collimator alignment. To ensure that every scan path 200 has the same length, the center 800 microns of RWG biosensor 102 must be the same in the x-direction. This constraint limits the radius of curvature of circular region 177 that truncates the outside corners of signal-grating region 102S and the reference-grating region 102R. Ensuring that every scan path 200 is the same length contributes to well-to-well assay consistency, and results in consistent noise performance for each well scan.

In an example, reference-grating region 102R can be defined by printing a polymer on the sensor surface using, for example, aerosol jet deposition. This polymer prevents covalent and ionic attachment of biomolecules during a biochemical assay. Due to the microplate tolerance stackup, a conventional RWG biosensor 102' as shown in FIG. 14A has a reference-grating region with a width $W_R$ (y-dimension) of at least 850 microns for a 2 mm×2 mm RWG biosensor. The aerosol jet follows a printing path 302 that prints in the long direction and that is rastered in the short direction and can include, for example, up to 16 passes or more for each reference-grating region 102R.

FIG. 14B illustrates an example asymmetric split-grating RWG biosensor 102 as described above in connection with FIG. 12A and FIG. 12B. The RWG biosensor 102 of FIG. 14B rotates the reference-grating region 102R by 90 degrees as compared to the conventional RWG biosensor 102' of FIG. 14A. This changes the optimum direction for ink-jet printing and rastering over printing path 302 (e.g., with a 50 micron wide jet). With the reduced width $W_R$ of the reference-grating region 102R as compared to the conventional RWG biosensor 102', the number of rasters for printing the reference-grating region can be reduced by half. This can result in, for example, a 50% decrease in the manufacturing cycle time.

In examples where the entirety of RWG biosensor 102 is located within well 175, it is advantageous that the RWG biosensor sensor to be a small as possible. As the size of RWG biosensor 102 decreases, the alignment tolerance for locating the RWG biosensor within well 175 increases. This alignment tolerance depends generally on two separate manufacturing processes. The first is the process of inserting the RWG biosensors in the wells, and this process must reliably locate the reference-grating region 102R and signal-grating region 102S relative to well edge 175E. The second is the assembly process, which involves aligning the RWG biosensors 102 within wells 175. Because both of these processes are mechanical, any increase in tolerance (or reduction in RWG biosensor size) improves process capability.

The assay response of optical reader systems tends to be the most consistent at well center 175C. If the liquid handling of the assay is not fully optimized, assay response variability across the well is likely. The assay variability is generally radial in nature and can be caused by a number of factors such as improper mixing during required steps. Non-parallel or uncalibrated pipette tip height can also contribute to low concentrations of assay components. Mishandling of the assay liquid can occur during the cell dispensing, protein immobilization, or compound addition steps. The resultant assay non-uniformity across the well is commonly referred to as "doming." For this reason, it can be advantageous that well center 175C be interrogated. The asymmetric split-grating RWG biosensor 102 can be advantageous in this regard because the non-resonant region 102D is not centered on well center 175C.

During assay troubleshooting, it can be helpful in embodiments to observe the assay response at well center 175C, and also at or near well edge 175E, and over the progression from the well center to the well edge. The asymmetric split-grating RWG biosensor 102 allows for more of the well center 175C to be interrogated than a symmetric split-grating design that is centered on well center 175C.

Future optical readers may be able to take advantage of RWG biosensors 102 having a greater sensor area than is presently used. However, a greater sensor area can be in conflict with the need to the minimize sensor area for ease of manufacturing. The addition of the rounded corners 102RC and 102SC for reference-grating region 102R and signal-grating region 102S, respectively (FIG. 12B), allows for a greater sensor area for a given tolerance as compared to the RWG bionsensor 102 of FIG. 12A. In embodiments, the addition of the round corners 102RC and 102SC results in a decrease in sensor area of less than 4%, but increases the tolerance by 26%. If an alignment tolerance of TOL=0.4 microns is achievable, the sensor area can be enlarged by 10% if rounded corners 102RC and 102SC are added. If the rounded corners 102RC and 102SC are problematic for manufacturing, they can be approximated without a substantial reduction in effect using a straight line or other type of curve instead of matching exactly the curvature of the circumscribed circle 177.

Table 1 provides example asymmetric split-grating RWG biosensor design parameters and corresponding alignment tolerances. In Table 1, biosensor design "1" corresponds to the first example asymmetric split-grating RWG biosensor configuration of FIG. 12A and biosensor design "2" corresponds to the second example asymmetric split-grating RWG biosensor of FIG. 12B. The "sensor height" is the dimension L, the "sensor width" is the dimension $W_S$, the "Reference and gap width" is $W_R$ D, the sensor area is given by $L \times ((W_R + D) + W_S)$, and the well area covered in percent is the sensor area divided by the well area times 100. TOL is the alignment tolerance as defined above.

TABLE 1

| Bio-sensor design | TOL (mm) | Sensor height (mm) | Signal width (mm) | Reference & gap width (mm) | Sensor area (mm²) | Well area covered (%) |
|---|---|---|---|---|---|---|
| 1 | 0.3 | 1.2 | 0.93 | 0.47 | 1.68 | 26.9 |
| 1 | 0.4 | 1.2 | 0.81 | 0.41 | 1.46 | 23.4 |
| 1 | 0.5 | 1.2 | 0.68 | 0.34 | 1.23 | 19.7 |
| 1 | 0.6 | 1.2 | 0.54 | 0.27 | 0.98 | 15.7 |
| 1 | 0.7 | 1.2 | 0.38 | 0.19 | 0.68 | 10.9 |
| 2 | 0.3 | 1.2 | 1.04 | 0.52 | 1.83 | 29.2 |
| 2 | 0.4 | 1.2 | 0.93 | 0.46 | 1.63 | 26.1 |

TABLE 1-continued

| Bio-sensor design | TOL (mm) | Sensor height (mm) | Signal width (mm) | Reference & gap width (mm) | Sensor area (mm²) | Well area covered (%) |
|---|---|---|---|---|---|---|
| 2 | 0.5 | 1.2 | 0.82 | 0.41 | 1.42 | 22.8 |
| 2 | 0.6 | 1.2 | 0.70 | 0.35 | 1.21 | 19.4 |
| 2 | 0.7 | 1.2 | 0.59 | 0.29 | 0.98 | 15.8 |

The two example asymmetric split-grating RWG biosensor designs can be scaled to other microplate formats including, for example, 96- and 1536-well microplate designs. Table 2 lists example asymmetric split-grating RWG biosensor sensor sizes for both the 96- and 1536-well microplate format. The notation "A/2" represents half-area microplate.

TABLE 2

| Microplate well format | Biosensor design | TOL (mm) | Sensor height (mm) | Signal width (mm) | Reference & gap width (mm) | Sensor area (mm²) | Well area covered (%) |
|---|---|---|---|---|---|---|---|
| 1536 | 1 | 0.25 | 0.8 | 0.51 | 0.25 | 0.61 | 24.2 |
| 384 | 1 | 0.50 | 1.2 | 0.68 | 0.34 | 1.23 | 19.7 |
| 384 | 2 | 0.50 | 1.2 | 0.82 | 0.41 | 1.42 | 22.8 |
| 96 A/2 | 1 | 0.50 | 2.1 | 1.40 | 0.70 | 4.41 | 27.7 |
| 96 A/2 | 2 | 0.50 | 2.1 | 1.70 | 0.85 | 5.04 | 31.7 |
| 96 | 1 | 0.50 | 3 | 2.18 | 1.09 | 9.83 | 31.5 |
| 96 | 2 | 0.50 | 3 | 2.62 | 1.31 | 11.0 | 35.4 |

Figure 15:
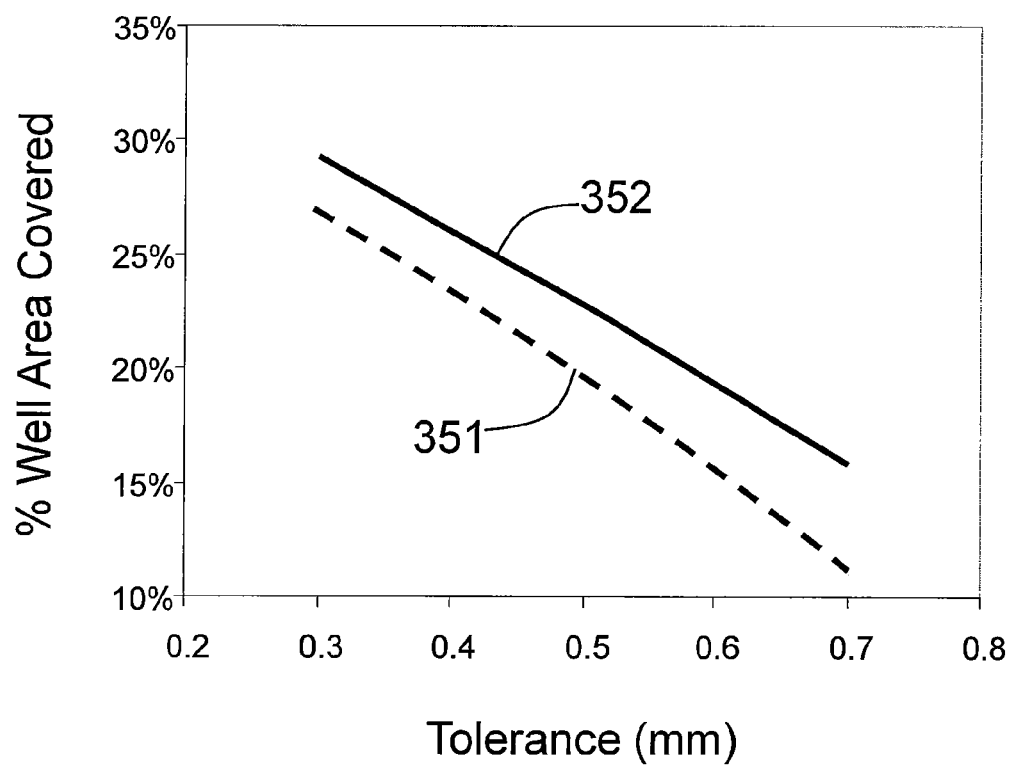
FIG. 15 plots the percent (%) well area covered versus the alignment tolerance for the two main types of asymmetric split-grating RWG biosensors disclosed herein.

FIG. 15 plots the "percent well area covered" versus the alignment tolerance (mm) for biosensor design 1 (curve 351) and biosensor design 2 (curve 352) of the asymmetric split-grating RWG biosensor 102. For a given tolerance requirement, biosensor design 2 provides a greater % well area coverage. For a given RWG biosensor area requirement, biosensor design 2 provides a greater well alignment tolerance.

It will be apparent to those skilled in the art that various modifications to the preferred embodiments of the disclosure as described herein can be made without departing from the scope of the disclosure as defined in the appended claims. Thus, the disclosure covers the modifications and variations provided they come within the scope of the appended claims and the equivalents thereto.

What is claimed is:

1. A system for reading a multi-grating resonant waveguide (RWG) biosensor, comprising:
   an optical reader system having a spatial resolution limit;
   the multi-grating resonant waveguide (RWG) biosensor operably arranged relative to the optical reader system;
   wherein the multi-grating RWG biosensor comprises:
   one or more signal-grating regions where chemical binding can occur;
   one or more reference-grating regions having a same grating structure as the one or more signal-grating regions but that are deactivated so that no chemical binding can occur, and wherein the one or more signal-grating regions do not overlap the one or more reference-grating regions; and
   a non-resonance region that spatially separates the one or more signal-grating regions, that spatially separates the one or more reference-grating regions, and that spatially separates the one or more reference-grating regions from the one or more signal-grating regions, the non-resonance region having a minimum width greater than the optical reader system spatial resolution limit.

2. The system of claim 1, having one signal-grating region and one reference-grating region.

3. The system of claim 1, wherein the signal-grating region has an area AS, the reference-grating region has an area AR, and wherein AS≠AR.

4. The system of claim 3, wherein AS>AR.

5. The system of claim 3 as arranged in a well having an edge and a center, and wherein the non-resonance region is not centered on the well center.

6. The system of claim 5, wherein the signal-grating region and the reference-grating region each have rounded corners adjacent the well edge.

7. The system of claim 1, comprising multiple signal-grating regions and a single reference-grating region.

8. The system of claim 1, wherein the non-resonance region has one of: no grating structure; a grating structure that has no waveguide coating; and a non-resonant-reflective coating.

9. The system of claim 1, wherein the one or more signal-grating regions and one or more reference-grating regions reside in a well of a microplate.

10. The system of claim 9, wherein the well supports different biological materials, and including multiple signal-grating regions each configured to operably support one of the different biological materials.

11. The system of claim 1, wherein the optical reader system generates a light spot having a diameter, and wherein the non-resonance region minimum width is at least greater than the diameter of the light spot.

12. The system of claim 1, further comprising:
a plurality of wells with each well configured to operably support a one of the multi-grating RWG biosensors; and
one multi-grating RWG biosensor operably disposed in each well.

13. The system claim 12, wherein at least one of the multi-grating RWG biosensors has an asymmetric split-grating configuration.

14. A method of measuring a signal resonant wavelength of a resonant waveguide (RWG) biosensor, comprising:
operably disposing in a well of a microplate the RWG bio sensor having spatially separated signal grating and reference-grating regions with a non-resonance region in between, wherein the reference-grating region has a same grating structure as the signal-grating region but is deactivated so that no chemical binding can occur, and wherein the signal-grating region does not overlap the reference-grating region;
irradiating the signal-grating region with an incident optical beam to generate reflected signal light without touching the reference-grating region, thereby generating reflected signal light and no reflected reference light; and
spectrally analyzing the reflected signal light to obtain the signal resonant wavelength.

15. The method of claim 14, further comprising:
irradiating the reference-grating region with the incident optical beam without touching the signal-grating region, thereby generating reflected reference light and no reflected signal light; and
spectrally analyzing the reflected reference light to obtain a reference resonant wavelength.

16. The method of claim 14, wherein the signal-grating region has a width and a length, and further comprising:
forming with the incident optical beam a light spot having a dimension larger than the signal-grating region width; and
wherein the signal scan path is linear along the length of the signal-grating region so that the entire signal-grating region is scanned.

17. The method of claim 14, wherein the signal-grating region has a width and a length, and further comprising:
forming with the incident optical beam a light spot having a dimension smaller than the signal-grating region width; and
wherein the signal scan path is zig-zag so that the substantially the entire signal-grating region is scanned.

18. The method of claim 14, further comprising forming the spatially separated signal grating and reference-grating regions by providing a grating having a unitary region and then removing a portion of the grating to form the non-resonant region.

19. The method of claim 14, further comprising forming the spatially separated signal grating and reference-grating regions by not forming a grating in the non-resonance region.

20. The method of claim 14, further comprising forming the spatially separated signal grating and reference-grating regions by forming a grating in the non-resonance region but not providing the grating with a waveguide coating.

21. The method of claim 14, wherein the well supports different biochemical substances, and further comprising providing multiple signal-grating regions each configured to operably support one of the different biological substances.

22. The method of claim 14, further comprising forming the signal-grating region to have an area AS, and forming the reference-grating region to have an area AR such that AS≠AR.

23. The method of claim 22, wherein AS>AR.

24. The method of claim 22, wherein the well has a center and wherein the non-resonance region is not centered on the well center.

25. The method of claim 22, wherein the well has an edge and wherein the signal-grating region and the reference-grating region each have a rounded corner adjacent the well edge.

26. A method of measuring a signal resonant wavelength of a resonant waveguide (RWG) biosensor using an optical reader having a spatial resolution limit, comprising:
operably disposing in a well of a microplate the RWG biosensor having spatially separated signal-grating and reference-grating regions with a non-resonance region in between wherein the reference-grating region has a same grating structure as the signal-grating region but that is deactivated so that no chemical binding can occur, and wherein the signal-grating region does not overlap the reference-grating region;
using an optical reader system having a resolution limit, simultaneously irradiating the signal-grating region, the reference-grating region and the non-resonance region with incident light to generate reflected light, wherein the non-resonance region has a minimum width greater than the spatial resolution limit;
establishing from the reflected light, a reflected signal component from the signal-grating region, a dark component from the non-resonance region, and a reflected reference component from the reference grating region; and
spectrally analyzing the reflected signal component to obtain the signal resonant wavelength.

27. The method of claim 26, further comprising simultaneously detecting the reflected light with an imaging sensor that forms a digital image, and wherein the establishing step includes digitally processing the digital image.

28. The method of claim 26, further comprising forming the non-resonance region by at least one of:
- forming no grating in the non-resonance region;
- providing a grating having a unitary region and then removing a portion of the grating;
- forming a grating in the non-resonance region but not providing a coating that causes the non-resonance region to have a resonance reflection at substantially the same wavelength as the signal-grating region;
- forming a grating, applying a waveguide coating thereon and then applying a masking layer over the waveguide coating to prevent resonance reflection from the grating and that defines the non-resonance region;
- forming a grating in the resonance wavelength region and then removing the grating, or a combination thereof.

29. The method of claim 26, further comprising operably disposing multiple RWG biosensors in respective multiple microplate wells.

30. The method of claim 26, further comprising forming the signal-grating region to have an area AS, and forming the reference-grating region to have an area AR such that AS≠AR.

31. The method of claim 30, wherein AS>AR.

32. The method of claim 30, wherein the well has a center and wherein the non-resonance region is not centered on the well center.

33. The method of claim 30, wherein the well has an edge and wherein the signal-grating region and the reference-grating region each have a rounded corner adjacent the well edge.

* * * * *